United States Patent [19]

Nam et al.

[11] Patent Number: 5,968,520
[45] Date of Patent: Oct. 19, 1999

[54] NATURAL TEAS FOR TAKING OFF THE EFFECTS OF DRINK AND PROCESS FOR THE PRODUCTION THEREOF

[76] Inventors: Jong Hyun Nam, 26-5, Koyo-dong, Songpa-ku, Seoul 138-110; Sam Rye Shin, 410-10, Taebang-dong, Tongjak-ku, Seoul 156-020, both of Rep. of Korea

[21] Appl. No.: 09/101,361
[22] PCT Filed: Apr. 3, 1997
[86] PCT No.: PCT/KR97/00058
  § 371 Date: Jul. 7, 1998
  § 102(e) Date: Jul. 7, 1998
[87] PCT Pub. No.: WO98/19687
  PCT Pub. Date: May 14, 1998

[30] Foreign Application Priority Data

Nov. 7, 1996 [KR] Rep. of Korea ................ 96/52651
Mar. 19, 1997 [KR] Rep. of Korea ................ 97/9266

[51] Int. Cl.⁶ .................................................. A01N 65/00
[52] U.S. Cl. ................... 424/195.1; 426/590; 426/597
[58] Field of Search ................ 424/195.1; 426/590, 426/597

[56] References Cited

U.S. PATENT DOCUMENTS 4,931,277  6/1990  Fontaine et al. .

FOREIGN PATENT DOCUMENTS 64-47721  2/1989  Japan .
6-263648  9/1994  Japan .
7-17847  1/1995  Japan .

OTHER PUBLICATIONS

Derwent Computer Abstract 97–478222 (44) WPIDS Gafurov et al RU 2076146, Mar. 27, 1997.

Derwent Computer Abstract 96–517057 (51) Kurmashina et al RU 2057173, Mar. 27, 1997.

Derwent Computer Abstract 96–496132 (49) Buslovich et al RU 2055874, Mar. 10, 1996.

*Primary Examiner*—Herbert J. Lilling
*Attorney, Agent, or Firm*—Renner, Otto, Boisselle & Sklar, P.L.L.

[57] ABSTRACT

Natural teas for taking off the effects of drink and getting rid of or curing the hangover. The teas can be prepared by using as the main raw materials extracts of leaves, stems or roots of alder and mountain ash or powders obtained by direct pulverization of leaves, stems or roots thereof, and optionally mixing the above extracts or powders with antidotal crude herb medicines including an extract of *fructus ligustic* fruit and an extract of *radix puerariae* at various mixing ratios. The effects of the teas for curing hangover are produced by taking the teas before or after drinking.

24 Claims, No Drawings

NATURAL TEAS FOR TAKING OFF THE EFFECTS OF DRINK AND PROCESS FOR THE PRODUCTION THEREOF

TECHNICAL FIELD

The present invention relates to natural teas for taking off the effects of drink and getting rid of or curing the so-called hangover and processes for preparing the same, and more particularly to natural teas comprising essentially extracts from alder and mountain ash(*Sorbus commixta* Hedl.) as well as processes for obtaining the teas.

BACKGROUND OF THE INVENTION

The inventors were interested in making natural and vegetal preparations for curing the hangover. After several tens of tests by using alders and mountain ashes, growing in Sosan, a region in Korea, inventors succeeded in making natural teas consisting of only vegetal ingredients, which are capable of curing the hangover, when taken before or after taking alcoholic drinks. The teas according to the present invention include extracts coming from leaves, stems, or roots of alder and mountain ash and further extracts coming from herb medicines being known to have functions of protecting the liver in the human body or detoxicating.

The hangover or the aftereffects of the heavy drink is thought to be influenced by toxic ethyl alcohols and/or acetaldehydes being accumulated in the liver from heavy alcoholic drinking. The hangover continues for hours due to the harmful effect of toxic ethyl alcohol and/or aldehyde on the liver, which causes the metabolism of the body to be deactivated, resulting in fatigue and exhaustion feeling of the whole body, feeling of having gas in the vowels, and vomiting.

Under a normal metabolism relating to ethyl alcohols in human body, the ethyl alcohols are absorbed into the stomach or the small intestines and thereafter, transferred to the liver through blood vessels. Alcohol dehydrogenase in the liver cells catalyzes the oxidation of ethyl alcohols to acetaldehydes, which in turn are decomposed into acetic acids by acetaldehyde dehydrogenase in the same cells. The resulting acetic acids are transferred to muscle and adipose tissues of the body and eventually converted to $CO_2$ and $H_2O$. Further, there are two types of acetaldehyde dehydrogenases: I—type one catalyzing the oxidation process of low concentrations of acetaldehydes and II—type one starting to activate the oxidation process only on high concentrations of acetaldehydes. Unfortunately, it is usual that Oriental people are lacking or short of the II—type acetaldehyde dehydrogenases and accordingly the oxidation of acetaldehydes is not so well activated that acetaldehydes and/or ethyl alcohols may not be decomposed and remain in the liver. The acetaldehydes and/or ethyl alcohols exceedingly accumulated in the liver disturb the normal metabolism and result in hangover. For diminishing or curing hangover, some herb or chemical medicines have been evaluated and used individually or in a group for hangover cure drinks.

A variety of herb medicines have been used for curing hangover and many liquid cures including such herb medicines are on the market. Those drinks may be taken alone before or after drinking, or mixed with strong alcoholic drinks to be taken. However, those beverages have some problems: one is to do more harm than good for curing the fatigue, feeling of having gas in the vowels, vomiting, or stomachache, and the other is the high price owing to the expensive medicinal herbs contained therein.

An object of the present invention is to provide natural teas or beverages which are capable of curing the hangover.

Another object of the present invention is to provide such hangover cure drinks with a low price.

DISCLOSURE OF INVENTION

The above objects are accomplished by providing natural teas (powdered or liquid) which consist mainly of extracts coming from the leaves, stems, or roots of alder and mountain ash, with extracts of *fructus ligustri* fruits and/or *radix puerariae* and/or gourds optionally mixed therein and precesses for preparing such natural teas.

Alders used for the present invention grow in low and moist places or valleys of mountains, or around small streams and their leaves, stems or roots are known to be rich in tannin being effective for protecting the stomach mucosa. Mountain ashes grow in a deep valley and their leaves and fruits contain a lot of Vitamin C, amino acids and carotenes. Extracts of mountain ashes are known to be good for scorbutus resulting from lacking of Vitamins and specifically the beta-carotene has the effect of clearing up cough and phlegm. *Fructus ligustri* fruits are effective for protecting the liver and the stomach.

In addition, extracts of *radix puerariae* may be added to improve the efficacy of curing hangover by the natural teas according to the present invention. *Radix puerariae*, a sweet and herbaceous vegetable, is known to have such functions that it helps patients recover from headache, and known to have excellent detoxicating functions by virtue of glycyrrhizin therein. Further, extracts of gourds may also be mixed in the natural teas of the present invention and ingredients thereof are said to work wonders on stimulation of urination.

As described above, medicinal properties of the respective vegetal ingredients used in the present invention are already known to the public. However, particular mixtures of those ingredients are believed to show remarkable synergistic effects. According to the present invention, for example, extracts of leaves, stems, or roots of alder are believed to strongly take part in the decomposition process of ethyl alcohols and/or acetaldehydes when extracts of leaves, stems, or roots of mountain ash are mixed therewith. Furthermore, extracts of mountain ash are believed to provide a supplement of Vitamin C which is apt to be insufficient due to consumption in the course of oxidation of ethyl alcohols, and specifically to contribute to removal of hangover by virtue of asparagine contained therein.

BEST MODES FOR CARRYING OUT THE INVENTION

The present invention will now be described in detail by way of examples.

EXAMPLE 1

Step 1. Preparation of Extract from Alder Leaves

After alder leaves were washed, dried and then chopped into small pieces, an extract of leaves was obtained by maceration at 70–80° C. for 4–6 hours in 30% ethyl alcohol extractant in an ordinary extractor. The resulting extract was cold spray-dried and thus an extractive powder was prepared.

Step 2. Preparation of Extract from Mountain Ash Leaves.

After mountain ash leaves were washed, dried and then chopped into small pieces, an extract of leaves was obtained by maceration at 70–80° C. for 4–6 hours in 30% ethyl alcohol extractant in an ordinary extractor. The resulting extract was cold spray-dried and thus an extractive powder was prepared.

Step 3. Preparation of a Natural Tea from the Extractive Powders

The extractive powder from alder leaves prepared in step 1 and the extractive powder from mountain ash leaves prepared in step 2 were mixed with the ratio of 10–80 parts by weight of the former and 20–90 parts by weight of the latter and then kept at 0–40° C. for 1–12 hours. Thereafter, the mixture was pulverized in a size of 50–150 meshes and thus, a natural tea according to the present invention was prepared.

EXAMPLE 2

Step 1. Preparation of Extract from Alder Stems

After alder stems were washed, dried and then chopped into small pieces, an extract of stems was obtained by maceration at 70–80° C. for 4–6 hours in 30% ethyl alcohol extractant in an ordinary extractor. The resulting extract was cold spray-dried and thus an extractive powder was prepared.

Step 2. Preparation of Extract from Mountain Ash Stems.

After mountain ash stems were washed, dried and then chopped into small pieces, an extract of stems was obtained by maceration at 70–80° C. for 4–6 hours in 30% ethyl alcohol extractant in an ordinary extractor. The resulting extract was cold spray-dried and thus an extractive powder was prepared.

Step 3. Preparation of a Natural Tea from the Extractive Powders.

The extractive powder from alder stems prepared in step 1 and the extractive powder from mountain ash stems prepared in step 2 were mixed with the ratio of 10–80 parts by weight of the former and 20–90 parts by weight of the latter and then kept at 0–40° C. for 1–12 hours. Thereafter, the mixture was pulverized in a size of 50–150 meshes and thus, a natural tea according to the present invention was prepared.

EXAMPLE 3

Step 1. Preparation of Extract from Alder Roots

After alder roots were washed, dried and then chopped into small pieces, an extract of roots was obtained by maceration at 70–80° C. for 4–6 hours in 30% ethyl alcohol extractant in an ordinary extractor. The resulting extract was cold spray-dried and thus an extractive powder was prepared.

Step 2. Preparation of Extract from Mountain Ash Leaves.

After mountain ash roots were washed, dried and then chopped into small pieces, an extract of roots was obtained by maceration at 70–80° C. for 4–6 hours in 30% ethyl alcohol extractant in an ordinary extractor. The resulting extract was cold spray-dried and thus an extractive powder was prepared.

Step 3. Preparation of a Natural Tea from the Extractive Powders.

The extractive powder from alder roots prepared in step 1 and the extractive powder from mountain ash roots prepared in step 2 were mixed with the ratio of 10–80 parts by weight of the former and 20–90 parts by weight of the latter and then kept at 0–40° C. for 1–12 hours. Thereafter, the mixture was pulverized in a size of 50–150 meshes and thus, a natural tea according to the present invention was prepared.

EXAMPLE 4

The extractive powder from alder leaves prepared in step 1 of the example 1 and the extractive powder from mountain ash stems prepared in step 2 of the example 2 were mixed with the ratio of 10–80 parts by weight of the former and 20–90 parts by weight of the latter and then kept at 0–40° C. for 1–12 hours. Thereafter, the mixture was pulverized in a size of 50–150 meshes and thus, a natural tea according to the present invention was prepared.

EXAMPLE 5

The extractive powder from alder leaves prepared in step 1 of the example 1 and the extractive powder from mountain ash roots prepared in step 2 of the example 3 were mixed with the ratio of 10–80 parts by weight of the former and 20–90 parts by weight of the latter and then kept at 0–40 ° C. for 1–12 hours. Thereafter, the mixture was pulverized in a size of 50–150 meshes and thus, a natural tea according to the present invention was prepared.

EXAMPLE 6

The extractive powder from alder stems prepared in step 1 of the example 2 and the extractive powder from mountain ash leaves prepared in step 2 of the example 1 were mixed with the ratio of 10–80 parts by weight of the former and 20–90 parts by weight of the latter and then kept at 0–40° C. for 1–12 hours. Thereafter, the mixture was pulverized in a size of 50–150 meshes and thus, a natural tea according to the present invention was prepared.

EXAMPLE 7

The extractive powder from alder stems prepared in step 1 of the example 2 and the extractive powder from mountain ash roots prepared in step 2 of the example 3 were mixed with the ratio of 10–80 parts by weight of the former and 20–90 parts by weight of the latter and then kept at 0–40° C. for 1–12 hours. Thereafter, the mixture was pulverized in a size of 50–150 meshes and thus, a natural tea according to the present invention was prepared.

EXAMPLE 8

The extractive powder from alder roots prepared in step 1 of the example 3 and the extractive powder from mountain ash leaves prepared in step 2 of the example 1 were mixed with the ratio of 10–80 parts by weight of the former and 20–90 parts by weight of the latter and then kept at 0–40° C. for 1–12 hours. Thereafter, the mixture was pulverized in a size of 50–150 meshes and thus, a natural tea according to the present invention was prepared.

EXAMPLE 9

The extractive powder from alder roots prepared in step 1 of the example 3 and the extractive powder from mountain ash stems prepared in step 2 of the example 2 were mixed with the ratio of 10–80 parts by weight of the former and 20–90 parts by weight of the latter and then kept at 0–40° C. for 1–12 hours. Thereafter, the mixture was pulverized in a size of 50–150 meshes and thus, a natural tea according to the present invention was prepared.

EXAMPLE 10

Step 1. Preparation of Extract from Fructus Ligustri Fruits

After *fructus ligustri* fruits were washed, dried and then chopped into small pieces, an extract of roots was obtained by maceration at 70–80° C. for 4–6 hours in 30% ethyl alcohol extractant in an ordinary extractor. The resulting extract was cold spray-dried and thus an extractive powder was prepared.

Step 2. Preparation of a Natural Tea from the Extractive Powders.

The extractive powder from alder leaves prepared in step 1 of the example 1 and the extractive powder from mountain ash leaves prepared in step 2 of the example 1 and the extractive powder from *fructus ligustri* fruits in step 1 of this example were mixed with the ratio of 10–70 parts by weight of the first and 20–80 parts by weight of the second and 2–10 parts by weight of the third and then kept at 0–40° C. for 1–12 hours. Thereafter, the mixture was pulverized in a size of 50–150 meshes and thus, a natural tea according to the present invention was prepared.

EXAMPLE 11

The extractive powder from alder stems prepared in step 1 of the example 2 and the extractive powder from mountain ash stems prepared in step 2 of the example 2 and the extractive powder from *fructus ligustri* fruits in step 1 of the example 9 were mixed with the ratio of 10–70 parts by weight of the first and 20–80 parts by weight of the second and 2–10 parts by weight of the third and then kept at 0–40° C. for 1–12 hours. Thereafter, the mixture was pulverized in a size of 50–150 meshes and thus, a natural tea according to the present invention was prepared.

EXAMPLE 12

The extractive powder from alder roots prepared in step 1 of the example 3 and the extractive powder from mountain ash roots prepared in step 2 of the example 3 and the extractive powder from *fructus ligustri* fruits in step 1 of the example 9 were mixed with the ratio of 10–70 parts by weight of the first and 20–80 parts by weight of the second and 2–10 parts by weight of the third and then kept at 0–40° C. for 1–12 hours. Thereafter, the mixture was pulverized in a size of 50–150 meshes and thus, a natural tea according to the present invention was prepared.

EXAMPLE 13

The extractive powder from alder leaves prepared in step 1 of the example 1 and the extractive powder from mountain ash stems prepared in step 2 of the example 2 and the extractive powder from *fructus ligustri* fruits in step 1 of example 9 were mixed with the ratio of 10–70 parts by weight of the first and 20–80 parts by weight of the second and 2–10 parts by weight of the third and then kept at 0–40° C. for 1–12 hours. Thereafter, the mixture was pulverized in a size of 50–150 meshes and thus, a natural tea according to the present invention was prepared.

EXAMPLE 14

The extractive powder from alder leaves prepared in step 1 of the example 1 and the extractive powder from mountain ash roots prepared in step 2 of the example 3 and the extractive powder from *fructus ligustri* fruits in step 1 of the example 9 were mixed with the ratio of 10–70 parts by weight of the first and 20–80 parts by weight of the second and 2–10 parts by weight of the third and then kept at 0–40° C. for 1–12 hours. Thereafter, the mixture was pulverized in a size of 50–150 meshes and thus, a natural tea according to the present invention was prepared.

EXAMPLE 15

The extractive powder from alder stems prepared in step 1 of the example 2 and the extractive powder from mountain ash leavess prepared in step 2 of the example 1 and the extractive powder from *fructus ligustri* fruits in step 1 of the example 9 were mixed with the ratio of 10–70 parts by weight of the first and 20–80 parts by weight of the second and 2–10 parts by weight of the third and then kept at 0–40° C. for 1–12 hours. Thereafter, the mixture was pulverized in a size of 50–150 meshes and thus, a natural tea according to the present invention was prepared.

EXAMPLE 16

The extractive powder from alder stems prepared in step 1 of the example 2 and the extractive powder from mountain ash roots prepared in step 2 of the example 3 and the extractive powder from *fructus ligustri* fruits in step 1 of example 9 were mixed with the ratio of 10–70 parts by weight of the first and 20–80 parts by weight of the second and 2–10 parts by weight of the third and then kept at 0–40° C. for 1–12 hours. Thereafter, the mixture was pulverized in a size of 50–150 meshes and thus, a natural tea according to the present invention was prepared.

EXAMPLE 17

The extractive powder from alder roots prepared in step 1 of the example 3 and the extractive powder from mountain ash leaves prepared in step 2 of the example 1 and the extractive powder from *fructus ligustri* fruits in step 1 of the example 9 were mixed with the ratio of 10–70 parts by weight of the first and 20–80 parts by weight of the second and 2–10 parts by weight of the third and then kept at 0–40° C. for 1–12 hours. Thereafter, the mixture was pulverized in a size of 50–150 meshes and thus, a natural tea according to the present invention was prepared.

EXAMPLE 18

The extractive powder from alder roots prepared in step 1 of the example 3 and the extractive powder from mountain ash stems prepared in step 2 of the example 2 and the extractive powder from *fructus ligustri* fruits in step 1 of the example 9 were mixed with the ratio of 10–70 parts by weight of the first and 20–80 parts by weight of the second and 2–10 parts by weight of the third and then kept at 0–40° C. for 1–12 hours. Thereafter, the mixture was pulverized in a size of 50–150 meshes and thus, a natural tea according to the present invention was prepared.

EXAMPLE 19

Step 1. Preparation of Extract from *Radix Puerariaes*

After *radix puerariaes* were washed, dried and then chopped into small pieces, an extract of roots was obtained by maceration at 70–80° C. for 4–6 hours in 30% ethyl alcohol extractant in an ordinary extractor. The resulting extract was cold spray-dried and thus an extractive powder was prepared.

Step 2. Preparation of a Natural Tea from the Extractive Powders.

The extractive powder from alder leaves prepared in step 1 of the example 1 and the extractive powder from mountain ash leaves prepared in step 2 of the example 1 and the extractive powder from *radix puerariaes* in step 1 of this example were mixed with the ratio of 10–65 parts by weight of the first and 20–70 parts by weight of the second and 15–40 parts by weight of the third and then kept at 0–40° C. for 1–12 hours. Thereafter, the mixture was pulverized in a size of 50–150 meshes and thus, a natural tea according to the present invention was prepared.

EXAMPLE 20

The extractive powder from alder stems prepared in step 1 of the example 2 and the extractive powder from mountain ash stems prepared in step 2 of the example 2 and the extractive powder from *radix puerariaes* in step 1 of the example 18 were mixed with the ratio of 10–70 parts by weight of the first and 20–80 parts by weight of the second and 15–40 parts by weight of the third and then kept at 0–40° C. for 1–12 hours. Thereafter, the mixture was pulverized in a size of 50–150 meshes and thus, a natural tea according to the present invention was prepared.

EXAMPLE 21

The extractive powder from alder roots prepared in step 1 of the example 3 and the extractive powder from mountain ash roots prepared in step 2 of the example 3 and the extractive powder from *radix puerariaes* in step 1 of the example 18 were mixed with the ratio of 10–70 parts by weight of the first and 20–80 parts by weight of the second and 15–40 parts by weight of the third and then kept at 0–40° C. for 1–12 hours. Thereafter, the mixture was pulverized in a size of 50–150 meshes and thus, a natural tea according to the present invention was prepared.

EXAMPLE 22

The extractive powder from alder leaves prepared in step 1 of the example 1 and the extractive powder from mountain ash stems prepared in step 2 of the example 2 and the extractive powder from *radix puerariaes* in step 1 of the example 18 were mixed with the ratio of 10–70 parts by weight of the first and 20–80 parts by weight of the second and 15–40 parts by weight of the third and then kept at 0–40° C. for 1–12 hours. Thereafter, the mixture was pulverized in a size of 50–150 meshes and thus, a natural tea according to the present invention was prepared.

EXAMPLE 23

The extractive powder from alder leaves prepared in step 1 of the example 1 and the extractive powder from mountain ash roots prepared in step 2 of the example 3 and the extractive powder from *radix puerariaes* in step 1 of the example 18 were mixed with the ratio of 10–70 parts by weight of the first and 20–80 parts by weight of the second and 2–10 parts by weight of the third and then kept at 0–40° C. for 1–12 hours. Thereafter, the mixture was pulverized in a size of 50–150 meshes and thus, a natural tea according to the present invention was prepared.

EXAMPLE 24

The extractive powder from alder stems prepared in step 1 of the example 2 and the extractive powder from mountain ash leavess prepared in step 2 of the example 1 and the extractive powder from *radix puerariaes* in step 1 of the example 18 were mixed with the ratio of 10–70 parts by weight of the first and 20–80 parts by weight of the second and 15–40 parts by weight of the third and then kept at 0–40° C. for 1–12 hours. Thereafter, the mixture was pulverized in a size of 50–150 meshes and thus, a natural tea according to the present invention was prepared.

EXAMPLE 25

The extractive powder from alder stems prepared in step 1 of the example 2 and the extractive powder from mountain ash roots prepared in step 2 of the example 3 and the extractive powder from *radix puerariaes* in step 1 of the example 18 were mixed with the ratio of 10–70 parts by weight of the first and 20–80 parts by weight of the second and 15–40 parts by weight of the third and then kept at 0–40° C. for 1–12 hours. Thereafter, the mixture was pulverized in a size of 50–150 meshes and thus, a natural tea according to the present invention was prepared.

EXAMPLE 26

The extractive powder from alder roots prepared in step 1 of the example 3 and the extractive powder from mountain ash leaves prepared in step 2 of the example 1 and the extractive powder from *radix puerariaes* in step 1 of the example 18 were mixed with the ratio of 10–70 parts by weight of the first and 20–80 parts by weight of the second and 15–40 parts by weight of the third and then kept at 0–40° C. for 1–12 hours. Thereafter, the mixture was pulverized in a size of 50–150 meshes and thus, a natural tea according to the present invention was prepared.

EXAMPLE 27

The extractive powder from alder roots prepared in step 1 of the example 3 and the extractive powder from mountain ash stems prepared in step 2 of the example 2 and the extractive powder from *radix puerariaes* in step 1 of the example 18 were mixed with the ratio of 10–70 parts by weight of the first and 20–80 parts by weight of the second and 15–40 parts by weight of the third and then kept at 0–40° C. for 1–12 hours. Thereafter, the mixture was pulverized in a size of 50–150 meshes and thus, a natural tea according to the present invention was prepared.

EXAMPLE 28

The extractive powder from alder leaves prepared in step 1 of the example 1 and the extractive powder from mountain ash leaves in step 2 of the example 1 and the extractive powder from *fructus ligustri* fruits in the step 1 of the example 9 and the extractive powder from *radix puerariaes* in step 1 of the example 18 were mixed with the ratio of 10–65 parts by weight of the first and 20–65 parts by weight of the second and 2–10 parts by weight of the third and 10–40 parts by weight of the forth and then kept at 0–40° C. for 1–12 hours. Thereafter, the mixture was pulverized in a size of 50–150 meshes and thus, a natural tea according to the present invention was prepared.

EXAMPLE 29

The extractive powder from alder stems prepared in step 1 of the example 2 and the extractive powder from mountain ash stems in step 2 of the example 2 and the extractive powder from *fructus ligustri* fruits in the step 1 of the example 9 and the extractive powder from *radix puerariaes* in step 1 of the example 18 were mixed with the ratio of 10–65 parts by weight of the first and 20–65 parts by weight of the second and 2–10 parts by weight of the third and 10–40 parts by weight of the forth and then kept at 0–40° C. for 1–12 hours. Thereafter, the mixture was pulverized in a size of 50–150 meshes and thus, a natural tea according to the present invention was prepared.

EXAMPLE 30

The extractive powder from alder roots prepared in step 1 of the example 3 and the extractive powder from mountain ash roots in step 2 of the example 3 and the extractive powder from *fructus ligustri* fruits in the step 1 of the example 9 and the extractive powder from *radix puerariaes* in step 1 of the example 18 were mixed with the ratio of 10–65 parts by weight of the first and 20–65 parts by weight of the second and 2–10 parts by weight of the third and 10–40 parts by weight of the forth and then kept at 0–40° C. for 1–12 hours. Thereafter, the mixture was pulverized in a size of 50–150 meshes and thus, a natural tea according to the present invention was prepared.

EXAMPLE 31

The extractive powder from alder leaves prepared in step 1 of the example 1 and the extractive powder from mountain ash stems in step 2 of the example 2 and the extractive powder from *fructus ligustri* fruits in the step 1 of the example 9 and the extractive powder from *radix puerariaes* in step 1 of the example 18 were mixed with the ratio of 10–65 parts by weight of the first and 20–65 parts by weight of the second and 2–10 parts by weight of the third and 10–40 parts by weight of the forth and then kept at 0–40° C. for 1–12 hours. Thereafter, the mixture was pulverized in a size of 50–150 meshes and thus, a natural tea according to the present invention was prepared.

EXAMPLE 32

The extractive powder from alder leaves prepared in step 1 of the example 1 and the extractive powder from mountain ash roots in step 2 of the example 3 and the extractive powder from *fructus ligustri* fruits in the step 1 of the example 9 and the extractive powder from *radix puerariaes* in step 1 of the example 18 were mixed with the ratio of 10–65 parts by weight of the first and 20–65 parts by weight of the second and 2–10 parts by weight of the third and 10–40 parts by weight of the forth and then kept at 0–40° C. for 1–12 hours. Thereafter, the mixture was pulverized in a size of 50–150 meshes and thus, a natural tea according to the present invention was prepared.

EXAMPLE 33

The extractive powder from alder stems prepared in step 1 of the example 2 and the extractive powder from mountain ash leaves in step 2 of the example 1 and the extractive powder from *fructus ligustri* fruits in the step 1 of the example 9 and the extractive powder from *radix puerariaes* in step 1 of the example 18 were mixed with the ratio of 10–65 parts by weight of the first and 20–65 parts by weight of the second and 2–10 parts by weight of the third and 10–40 parts by weight of the forth and then kept at 0–40° C. for 1–12 hours. Thereafter, the mixture was pulverized in a size of 50–150 meshes and thus, a natural tea according to the present invention was prepared.

EXAMPLE 34

The extractive powder from alder stems prepared in step 1 of the example 2 and the extractive powder from mountain ash roots in step 2 of the example 3 and the extractive powder from *fructus ligustri* fruits in the step 1 of the example 9 and the extractive powder from *radix puerariaes* in step 1 of the example 18 were mixed with the ratio of 10–65 parts by weight of the first and 20–65 parts by weight of the second and 2–10 parts by weight of the third and 10–40 parts by weight of the forth and then kept at 0–40° C. for 1–12 hours. Thereafter, the mixture was pulverized in a size of 50–150 meshes and thus, a natural tea according to the present invention was prepared.

EXAMPLE 35

The extractive powder from alder roots prepared in step 1 of the example 3 and the extractive powder from mountain ash leaves in step 2 of the example 1 and the extractive powder from *fructus ligustri* fruits in the step 1 of the example 9 and the extractive powder from *radix puerariaes* in step 1 of the example 18 were mixed with the ratio of 10–65 parts by weight of the first and 20–65 parts by weight of the second and 2–10 parts by weight of the third and 10–40 parts by weight of the forth and then kept at 0–40° C. for 1–12 hours. Thereafter, the mixture was pulverized in a size of 50–150 meshes and thus, a natural tea according to the present invention was prepared.

EXAMPLE 36

The extractive powder from alder roots prepared in step 1 of the example 3 and the extractive powder from mountain ash stems in step 2 of the example 2 and the extractive powder from *fructus ligustri* fruits in the step 1 of the example 9 and the extractive powder from *radix puerariaes* in step 1 of the example 18 were mixed with the ratio of 10–65 parts by weight of the first and 20–65 parts by weight of the second and 2–10 parts by weight of the third and 10–40 parts by weight of the forth and then kept at 0–40° C. for 1–12 hours. Thereafter, the mixture was pulverized in a size of 50–150 meshes and thus, a natural tea according to the present invention was prepared.

The various parameters of the technical processes described above are provided by way of examples and are not restrictive. For example, ordinary extraction by maceration in the above examples 1–36 may be conducted at low or high temperatures. When the extraction is carried out at the low temperatures of 30° C.–80° C., the time of maceration may vary from 1 hour to 10 hours. Also, the extraction by maceration may be conducted at high temperatures below 150° C. with the pressure of 2–3 atm. Though the 30% ethyl alcohol was used as an extractant, pure water or 10–70% ethyl alcohols may be used as a substitute on the same conditions. Furthermore, powders directly pulverized from leaves, stems, or roots of alders, mountain ashes, *fructus ligustri* fruits and *radix puerariaes* may be used as substitutes for extractive powders in the corresponding preparation steps of natural teas in the above examples. Also, some herb medicines such as jujubes or licorice roots may be added into natural teas prepared in the examples 1–36 for improving sweet tastes of natural teas according to the present invention. Some steps, for example, concentrating of extracts, may be included in the processes described in the examples 1–36 and thus, more raw materials than in case of making extractive powders can be disposed.

According to the tests made, the inventors confirmed that respective extracts of leaves, stems, or roots of alder or mountain ash show almost the same effects on curing the hangover and that the efficacy of the teas of the present invention has little with the specific parts of alder or mountain ash. Therefore, inventors believe that the efficacy of natural teas according to the present invention comes from the particular mixing ratios of extracts of the materials, irrespective of the specific collected parts of them.

The effect of the teas of the present invention can also be realized by the teas according to the following examples, in which small pieces of leaves, stems, or roots of alder and mountain ash were mixed altogether and then extracts were obtained from the mixtures.

EXAMPLE 37

Alder leaves and mountain ash leaves were respectively washed and dried and then, chopped into small pieces.

Those small pieces of the alder leaves and the mountain ash leaves were mixed with the ratio of 10–80 parts by weight of the former and 20–90 parts by weight of the latter. Then, an extract of the mixture was obtained by maceration at 70–80° C. for 4–6 hours in 30% ethyl alcohol extractant in an ordinary extractor. The extract was spray-dried and then pulverized in a size of 50–150 meshes.

EXAMPLE 38

Alder stems and mountain ash stems were respectively washed and dried and then, chopped into small pieces.

Those small pieces of the alder stems and the mountain ash stems were mixed with the ratio of 10–80 parts by weight of the former and 20–90 parts by weight of the latter. Then, an extract of the mixture was obtained by maceration at 70–80° C. for 4–6 hours in 30% ethyl alcohol extractant in an ordinary extractor. The extract was spray-dried and then pulverized in a size of 50–150 meshes.

EXAMPLE 39

Alder roots and mountain ash roots were respectively washed and dried and then, chopped into small pieces.

Those small pieces of the alder roots and the mountain ash roots were mixed with the ratio of 10–80 parts by weight of the former and 20–90 parts by weight of the latter. Then, an extract of the mixture was obtained by maceration at 70–80° C. for 4–6 hours in 30% ethyl alcohol extractant in an ordinary extractor. The extract was spray-dried and then pulverized in a size of 50–150 meshes.

EXAMPLE 40

Alder leaves and mountain ash stems were respectively washed and dried and then, chopped into small pieces.

Those small pieces of the alder leaves and the mountain ash stems were mixed with the ratio of 10–80 parts by weight of the former and 20–90 parts by weight of the latter. Then, an extract of the mixture was obtained by maceration at 70–80° C. for 4–6 hours in 30% ethyl alcohol extractant in an ordinary extractor. The extract was spray-dried and then pulverized in a size of 50–150 meshes.

EXAMPLE 41

Alder leaves and mountain ash roots were respectively washed and dried and then, chopped into small pieces.

Those small pieces of the alder leaves and the mountain ash roots were mixed with the ratio of 10–80 parts by weight of the former and 20–90 parts by weight of the latter. Then, an extract of the mixture was obtained by maceration at 70–80° C. for 4–6 hours in 30% ethyl alcohol extractant in an ordinary extractor. The extract was spray-dried and then pulverized in a size of 50–150 meshes.

EXAMPLE 42

Alder stems and mountain ash leaves were respectively washed and dried and then, chopped into small pieces.

Those small pieces of the alder stems and the mountain ash leaves were mixed with the ratio of 10–80 parts by weight of the former and 20–90 parts by weight of the latter. Then, an extract of the mixture was obtained by maceration at 70–80° C. for 4–6 hours in 30% ethyl alcohol extractant in an ordinary extractor. The extract was spray-dried and then pulverized in a size of 50–150 meshes.

EXAMPLE 43

Alder stems and mountain ash roots were respectively washed and dried and then, chopped into small pieces.

Those small pieces of the alder stems and the mountain ash roots were mixed with the ratio of 10–80 parts by weight of the former and 20–90 parts by weight of the latter. Then, an extract of the mixtures was obtained by maceration at 70–80° C. for 4–6 hours in 30% ethyl alcohol extractant in an ordinary extractor. The extract was spray-dried and then pulverized in a size of 50–150 meshes.

EXAMPLE 44

Alder roots and mountain ash leaves were respectively washed and dried and then, chopped into small pieces.

Those small pieces of the alder roots and the mountain ash leaves were mixed with the ratio of 10–80 parts by weight of the former and 20–90 parts by weight of the latter. Then, an extract of the mixtures was obtained by maceration at 70–80° C. for 4–6 hours in 30% ethyl alcohol extractant in an ordinary extractor. The extract was spray-dried and then pulverized in a size of 50–150 meshes.

EXAMPLE 45

Alder roots and mountain ash stems were respectively washed and dried and then, chopped into small pieces.

Those small pieces of the alder roots and the mountain ash stems were mixed with the ratio of 10–80 parts by weight of the former and 20–90 parts by weight of the latter. Then, an extract of the mixture was obtained by maceration at 70–80° C. for 4–6 hours in 30% ethyl alcohol extractant in an ordinary extractor. The extract was spray-dried and then pulverized in a size of 50–150 meshes.

The following examples are for the teas according to the present invention further comprising fructus lingustri fruits, in which small pieces of *fructus ligustri* fruits are added to the mixture of small pieces of leaves, stems, or roots of alder and mountain ash and then, extractive powders are obtained. Because the specific collected parts of alder or mountain ash hardly affect the efficacy of natural teas according to the present invention, as described above, only selected examples are disclosed.

EXAMPLE 46

Alder leaves and mountain ash leaves were respectively washed and dried and then, chopped into small pieces.

*Fructus ligustri* fruits were washed and dried and then, chopped into small pieces.

Those small pieces of the alder leaves, the mountain ash leaves and *fructus ligustri* fruits were mixed with the ratio of 10–70 parts by weight of the first and 20–80 parts by weight of the second and 2–10 parts by weight of the third. Then, an extract of the mixture was obtained by maceration at 70–80° C. for 4–6 hours in 30% ethyl alcohol extractant in an ordinary extractor. The extract was spray-dried and then pulverized in a size of 50–150 meshes.

EXAMPLE 47

Alder stems and mountain ash stems were respectively washed and dried and then, chopped into small pieces.

*Fructus ligustri* fruits were washed and dried and then, chopped into small pieces.

Those small pieces of the alder stems, the mountain ash stems and *fructus ligustri* fruits were mixed with the ratio of 10–70 parts by weight of the first and 20–80 parts by weight of the second and 2–10 parts by weight of the third. Then, an extract of the mixture was obtained by maceration at 70–80° C. for 4–6 hours in 30% ethyl alcohol extractant in an ordinary extractor. The extract was spray-dried and then pulverized in a size of 50–150 meshes.

EXAMPLE 48

Alder roots and mountain ash roots were respectively washed and dried and then, chopped into small pieces.

*Fructus ligustri* fruits were washed and dried and then, chopped into small pieces.

Those small pieces of the alder roots, the mountain ash roots and *fructus ligustri* fruits were mixed with the ratio of 10–70 parts by weight of the first and 20–80 parts by weight of the second and 2–10 parts by weight of the third. Then, an extract of the mixture was obtained by maceration at 70–80° C. for 4–6 hours in 30% ethyl alcohol extractant in an ordinary extractor. The extract was spray-dried and then pulverized in a size of 50–150 meshes.

The following examples are for the teas according to the present invention further comprising *radix puerariaes* or *fructus ligustri* fruits and radix puerariaes, in which small pieces of *radix puerariaes* or *fructus ligustri* fruits and *radix puerariaes* are added to the mixture of small pieces of leaves, stems, or roots of alder and mountain ash and then, extractive powders are obtained.

EXAMPLE 49

Alder leaves and mountain ash leaves were respectively washed and dried and then, chopped into small pieces.

*Radix puerariaes* were washed and dried and then, chopped into small pieces.

Those small pieces of the alder leaves, the mountain ash leaves and *radix puerariaes* were mixed with the ratio of 10–65 parts by weight of the first and 20–70 parts by weight of the second and 15–40 parts by weight of the third. Then, an extract of the mixture was obtained by maceration at 70–80° C. for 4–6 hours in 30% ethyl alcohol extractant in an ordinary extractor. The extract was spray-dried and then pulverized in a size of 50–150 meshes.

EXAMPLE 50

Alder stems and mountain ash stems were respectively washed and dried and then, chopped into small pieces.

*Radix puerariaes* were washed and dried and then, chopped into small pieces.

Those small pieces of the alder stems, the mountain ash stems and *radix puerariaes* were mixed with the ratio of 10–65 parts by weight of the first and 20–70 parts by weight of the second and 15–40 parts by weight of the third. Then, an extract of the mixture was obtained by maceration at 70–80° C. for 4–6 hours in 30% ethyl alcohol extractant in an ordinary extractor. The extract was spray-dried and then pulverized in a size of 50–150 meshes.

EXAMPLE 51

Alder roots and mountain ash roots were respectively washed and dried and then, chopped into small pieces.

*Radix puerariaes* were washed and dried and then, chopped into small pieces.

Those small pieces of the alder roots, the mountain ash roots and *radix puerariaes* were mixed with the ratio of 10–65 parts by weight of the first and 20–70 parts by weight of the second and 15–40 parts by weight of the third. Then, an extract of the mixture was obtained by maceration at 70–80° C. for 4–6 hours in 30% ethyl alcohol extractant in an ordinary extractor. The extract was spray-dried and then pulverized in a size of 50–150 meshes.

EXAMPLE 52

Alder leaves, mountain ash leaves, *fructus ligustri* fruits and radix puerariaes were respectively washed and dried and then, chopped into small pieces.

Those small pieces of the alder leaves, the mountain ash leaves, *fructus ligustri* fruits and *radix puerariaes* were mixed with the ratio of 10–65 parts by weight of the first and 10–65 parts by weight of the second and 2–10 parts by weight of the third and 2–10 parts by weightof the forth. Then, an extract of the mixture was obtained by maceration at 70–80° C. for 4–6 hours in 30% ethyl alcohol extractant in an ordinary extractor. The extract was spray-dried and then pulverized in a size of 50–150 meshes.

EXAMPLE 53

Alder stems, mountain ash stems, *fructus ligustri* fruits and radix puerariaes were respectively washed and dried and then, chopped into small pieces.

Those small pieces of the alder stems, the mountain ash stems, *fructus ligustri* fruits and *radix puerariaes* were mixed with the ratio of 10–65 parts by weight of the first and 10–65 parts by weight of the second and 2–10 parts by weight of the third and 2–10 parts by weight of the forth. Then, an extract of the mixture was obtained by maceration at 70–80° C. for 4–6 hours in 30% ethyl alcohol extractant in an ordinary extractor. The extract was spray-dried and then pulverized in a size of 50–150 meshes.

EXAMPLE 54

Alder roots, mountain ash roots, *fructus ligustri* fruits and radix puerariaes were respectively washed and dried and then, chopped into small pieces.

Those small pieces of the alder roots, the mountain ash roots, *fructus ligustri* fruits and *radix puerariaes* were mixed with the ratio of 10–65 parts by weight of the first and 10–65 parts by weight of the second and 2–10 parts by weight of the third and 2–10 parts by weight of the forth. Then, an extract of the mixture was obtained by maceration at 70–80° C. for 4–6 hours in 30% ethyl alcohol extractant in an ordinary extractor. The extract was spray-dried and then pulverized in a size of 50–150 meshes.

Ordinary extraction by maceration in the examples 37–54 may be conducted at low or high temperatures. When the extraction is carried out at the low temperatures of 30° C.–80° C., 1–10 hours of maceration may be required. On the other hand, if at the high temperatures below 150° C., the pressures of 2–3 atm. may be applied in the extraction procedures.

Pure water or 10–70% ethyl alcohol extractant may also be used on the same conditions during the course of extraction by maceration in the examples 37–54. Further, some herb medicines such as jujubes or licorice roots may be added to the natural teas prepared in the examples 37–54, for getting better sweetness of the natural teas according to the present invention. Concentrating processes of extracts may be involved in the examples 37–54, if necessary, which may lead to disposing of a lot more materials. Also, natural tea concentrates may be prepared from the natural tea powders obtained in the above examples 1–54. After 10–20 parts by weight of natural tea powders were put in 100 parts by weight of cool water for 1–10 hours, the mixture may be decocted for 1–12 hours at 50–100° C. in an ordinary decocting device to make the natural tea concentrates according to the present invention.

In the processes for preparing natural tea powders disclosed in examples 1 to 54 and for natural tea concentrates, an extract or an extractive powder of gourds may be further added to the natural teas for improving urination of drinker. The extract or the extractive powder thereof may be obtained if the same processes for the extract or the extractive powder of alder leaves are applied to gourds.

As described above, the specific parts collected from alder or mountain ash were not recognized as critical variables to determine the efficacy of the natural teas of the present invention. Accordingly, the term of extracts of alder or mountain ash will hereinafter covers extracts of the leaves, stems or roots of alder or mountain ash, respectively.

Test 1

In order to confirm the decomposition rates of 30% or 50% ethyl alcohols by using the natural teas according to the present invention, 0.1 l samples of the natural tea prepared as shown in Table 1 were mixed respectively with 1 l of 30% or 50% ethyl alcohol. As the more alcohols are decomposed, the less drinkers feel hangover after drinking, the alcohol decomposition rate is presented for the purpose of demonstrating the effect of the teas of the present invention. Further, the decomposition rate is easily measured by an ordinary alcohol hydrometer.

100 parts by weight of the extractive powders of alder, mountain ash and optionally *fructus ligustri* fruits and/or *radix puerariae* with various mixing ratios were put in 1200 cc of water and thus samples A to M were prepared as shown in Table 1.

Table 2 shows the degree of decomposition of ethyl alcohols according to the time elapsed after 0.1 l samples A to M of the teas were mixed with 1 l of 30% or 50% ethyl alcohol of respectively.

TABLE 1

Compositions of samples prepared

| Component Samples | extractive powder from alder (parts by weight) | extractive mountain ash from alder (parts by weight) | extractive fructus lingustri fruit (parts by weight) | extractive radix puerarie (parts by weight) |
|---|---|---|---|---|
| A | 10 | 90 | | |
| B | 50 | 50 | | |
| C | 80 | 20 | | |
| D | 10 | 80 | 10 | |
| E | 43 | 55 | 2 | |
| F | 70 | 20 | 10 | |
| G | 10 | 70 | | 20 |
| H | 20 | 40 | | 40 |
| I | 65 | 20 | | 15 |
| J | 10 | 65 | 2 | 23 |
| K | 20 | 40 | 10 | 30 |
| L | 65 | 20 | 5 | 10 |
| M | 25 | 30 | 5 | 40 |

TABLE 2

Ethyl alcohol concentrations (%) changed according to the time elapsed.

| samples | alcohol concentrations | 5 mins. | 10 mins. | 30 mins. | 24 hrs. | 48 hrs. |
|---|---|---|---|---|---|---|
| A | 30% | 27 | 26 | 8 | 5 | |
|   | 50% | 47 | 39 | 15 | 9 | |

TABLE 2-continued

Ethyl alcohol concentrations (%) changed according to the time elapsed.

| samples | alcohol concentrations | 5 mins. | 10 mins. | 30 mins. | 24 hrs. | 48 hrs. |
|---|---|---|---|---|---|---|
| B | 30% | 23 | 21 | 5 | 3 | |
|   | 50% | 42 | 36 | 11 | 7 | 5 |
| C | 30% | 29 | 28 | 9 | 6 | |
|   | 50% | 48 | 41 | 20 | 9 | 8 |
| D | 30% | 28 | 26 | 9 | 6 | |
|   | 50% | 45 | 38 | 14 | 11 | 8 |
| E | 30% | 25 | 22 | 7 | 5 | |
|   | 50% | 43 | 37 | 13 | 8 | 7 |
| F | 30% | 28 | 27 | 12 | 7 | |
|   | 50% | 46 | 38 | 17 | 13 | 8 |
| G | 30% | 27 | 24 | 7 | 6 | |
|   | 50% | 47 | 38 | 15 | 13 | 11 |
| H | 30% | 26 | 23 | 5 | 4 | |
|   | 50% | 43 | 38 | 13 | 10 | 7 |
| I | 30% | 27 | 25 | 12 | 8 | |
|   | 50% | 48 | 40 | 18 | 13 | 11 |
| J | 30% | 27 | 26 | 12 | 9 | |
|   | 50% | 47 | 41 | 18 | 11 | 8 |
| K | 30% | 24 | 22 | 8 | 5 | |
|   | 50% | 44 | 39 | 12 | 10 | 8 |
| L | 30% | 25 | 22 | 9 | 6 | |
|   | 50% | 44 | 40 | 12 | 11 | 9 |
| M | 30% | 29 | 27 | 11 | 8 | |
|   | 50% | 48 | 43 | 20 | 13 | 10 |

The above test results show that the natural teas according to the present invention remarkably decrease the ethyl alcohol contents with the time elapsed after the teas have been taken. Thus, we can see that the teas according to the present invention will contribute to curing the hangover caused by the ethyl alcohols absorbed into the system and/or the acetaldehydes developed from the ethyl alcohols.

Industrial Applicability

According to the present invention, natural teas, powdered or liquid, with the efficacy of sobering the drinker up and curing the hangover may be prepared with a low price and contribute to prevention of liver diseases by relieving the liver from the burden of decomposing alcohols absorbed therein.

We claim:

1. A tea comprising 10–80 parts by weight of an alder extract and 20–90 parts by weight of a mountain ash extract, the alder extract and the mountain ash extract being prepared from leaves, stems or roots of alder or mountain ash by ordinary extraction processes at 70–80° C. for 4–6 hours in an extractant.

2. A tea according to claim 1, the extractant is 30% ethyl alcohol or pure water.

3. A tea according to claim 1, further comprising a fructus lingusti fruit extract.

4. A tea according to claim 1, further comprising a radix puerariae extract.

5. A tea according to claim 1, further comprising a gourd extract.

6. A tea according to claim 3, further comprising a *radix puerariae* extract.

7. A tea according to claim 6, further comprising a gourd extract.

8. A tea according to claim 3, wherein the fructus lingusti fruit extract is prepared by an ordinary extraction porcess at 70–80° C. for 4–6 hours in a 30% ethyl alcohol.

9. A tea according to claim 4, wherein the *radix puerariae* extract is prepared by an ordinary extraction process at 70–80° C. for 4–6 hours in a 30% ethyl alcohol.

10. A tea according to claim 3, wherein 10–70 parts by weight of the alder extract and 20–80 parts by weight of the mountain ash extract are mixed with 2–10 parts by weight of the fructus lingusti fruit extract.

11. A tea according to claim 4, wherein 10–65 parts by weight of the alder extract and 20–70 parts by weight of the mountain ash extract are mixed with 15–40 parts by weight of the *radix puerariae* extract.

12. A tea according to claim 6, wherein 10–65 parts by weight of the alder extract and 20–65 parts by weight of the mountain ash extract are mixed with 2–10 parts by weight of the fructus lingusti fruit extract and 10–40 parts by weight of the *radix puerariae* extract.

13. A process for preparing a tea, comprising the steps of:
   obtaining an extract from leaves, stems, or roots of alder by an ordinary extraction process at 70–80° C. for 4–6 hours in an extractant;
   obtaining an extract from leaves, stems or roots of mountain ash by an ordinary extraction process at 70–80° C. for 4–6 hours in an extractant;
   mixing the alder extract with the mountain ash extract; and pulverizing the mixture into a powder.

14. A process for preparing a tea according to claim 13, wherein the extractant is 30% ethyl alcohol or pure water.

15. A process for preparing a tea according to claim 13, wherein the mixing step includes mixing 10–80 parts by weight of the alder extract with 20–90 parts by weight of the mountain ash extract and keeping the mixture at 0° C.–40° C. for 1–12 hours.

16. A process for preparing a tea according to claim 13, wherein the pulverizing step makes the powder in a size of 50–150 meshes.

17. A process for preparing a tea according to claim 13, wherein a fructus ligusti fruit extract and a *radix puerariae* extract are further added in the mixing step.

18. A process for preparing a tea according to claim 17, wherein the mixing step include mixing 10–65 parts by weight of the alder extract and 20–65 parts by weight of the mountain ash extract with 2–10 parts by weight of the fructus lingusti fruit extract and 10–40 parts by weight of the *radix puerariae* extract and keeping the mixture at 0° C.–40° C. for 1–12 hours.

19. A process for preparing a tea according to claim 13, wherein a gourd extract is further added in the mixing step.

20. A process for preparing a tea according to claim 13, further comprising the steps of keeping 10–20 parts of the pulverized mixture in 100 parts by weight of cool water and decocting the mixture at 50–100° C. for 1–12 hours, for making a concentrated natural tea.

21. A process for preparing a tea, comprising the steps of:
   mixing small pieces of leaves, stems or roots of alder with small pieces of leaves, stems or root of mountain ash;
   obtaining an extract of the resultant mixture by an ordinary extraction process at 70–80° C. for 4–6 hours in an extractant; and drying the extract.

22. A process for preparing a tea according to claim 21, wherein small pieces of fructus ligustic fruit are added in the mixing step.

23. A process for preparing a tea according to claim 21, wherein small pieces of *radix puerariae* are further added in the mixing step.

24. A process for preparing a tea according to claim 23, wherein small pieces of gourd are further added in the mixing step.

* * * * *